United States Patent [19]

Lilla

[11] Patent Number: 4,497,316

[45] Date of Patent: Feb. 5, 1985

[54] CANTILEVERED SUSPENSION SLING

[76] Inventor: James A. Lilla, 4431 Ashton Dr., Sacramento, Calif. 95825

[21] Appl. No.: 394,445

[22] Filed: Jul. 1, 1982

[51] Int. Cl.³ .............................................. A61F 5/10
[52] U.S. Cl. ...................................... 128/94; 128/77; 128/87 R
[58] Field of Search ............... 128/94, 87 R, 87 B, 128/82, 149, 133, 155, 165, 77; 224/149, 150, 201, 208, 185, 196, 197, 205-206, 257-259, 265, 910, 913, 916, 153; 3/12.3

[56] References Cited

U.S. PATENT DOCUMENTS

| 2,460,589 | 2/1949 | Lewis | 128/94 |
| 2,980,426 | 4/1961 | Johnson | 128/77 |
| 3,815,588 | 6/1974 | Klausner | 128/94 X |
| 4,198,964 | 4/1980 | Honneffer | 128/94 X |
| 4,232,664 | 11/1980 | Blatt | 128/94 |

Primary Examiner—Robert A. Hafer
Assistant Examiner—Chris Coppens
Attorney, Agent, or Firm—Cushman, Darby & Cushman

[57] ABSTRACT

An arm sling includes a semi-rigid trough which partially encircles and supports a patient's forearm, wrist, and hand. A yoke is connected to the sides of the trough at a location away from the distal end. An adjustable-length strap extends upward from the yoke over the front of the patient's ipsilateral shoulder, diagonally across the patient's back, and transversly across the front of the patient's body to an attachment point on the trough near the patient's elbow. An elbow piece adjustably fixed to the trough accommodates various elbow angles and arm widths. The yoke supports the patient's forearm, wrist, and hand in a cantilevered fashion at various elevations, while not interfering appreciably with lateral movement of the distal end of the trough and rotation of the patient's upper arm at the shoulder joint.

4 Claims, 6 Drawing Figures

CANTILEVERED SUSPENSION SLING

BACKGROUND OF THE INVENTION

1. Field of the Invention

This invention relates to medical devices and, more particularly, to arm slings and methods of supporting a patient's arm.

2. Prior Art

Previously, a variety of general-purpose arm slings have been available. These slings include those having a soft, very flexible envelope, or closed trough, which surrounds and provides some support to the patient's forearm. In some cases, slings of this design prevent easy access to the patient's arm for theraputic purposes. To provide support to the distal end of the patient's forearm, that is, the wrist and hand, this type of sling is supported by a strap attached near the distal end of the fabric envelope and extending around the patient's neck. The proximal portion of the supporting strap for a flexible envelope continues over or behind the shoulder of the arm being supported, that is, the ipsilateral shoulder. In such an arrangement the weight being supported often presses on the side or back of the neck of the individual. Moreover, the result is that the patient's arm extends across the front of the patients chest, rotation of the patient's upper arm at the shoulder joint is severely restricted, and elevation of the distal end of the patient's arm is difficult and uncomfortable. That is, if the strap is tightened to elevate the patient's hand and wrist, the arm is pulled even more tightly to the chest. The height of hand elevation is limited by how tightly the strap can be made around the neck, how closely the trough can be brought to the neck, and whether or not the distal end of the flexible envelope collapses in the process of elevation, thus allowing the hand and wrist to droop.

Examples of various types of arm slings having soft, flexible envelopes and/or prior methods of suspension, are disclosed in U.S. Pat. Nos. 980,464; 3,103,216; 3,433,221; 4,232,664; and 4,285,337.

Specific apparatus for rigidly fixing a patient's wrist and hand in position on a relatively rigid forearm supporting member are disclosed in U.S. Pat. Nos. 3,815,588 and 4,214,579, both of which apparatus include support straps extending over the patient's opposite, that is, contralateral, shoulder, which prevents rotation of the patient's upper arm at the shoulder joint.

A variety of arm sling positions are desired depending upon the patient's particular injury or disability; so that an arm sling which provides for a wide range of positions depending upon the needs of a particular patient is very desirable. These positions include one in which the upper arm is substantially vertical while the forearm is substantially horizontal and extends across the patient's lower chest. Another position is one in which the upper arm is still vertical but the forearm is elevated from the elbow at approximately 45 degrees and extends across the front of the patient's chest, keeping the patient's hand above the heart to prevent edema.

Some prior art slings include an elbow pocket to help support the arm and to keep the patient's arm in the fabric envelope when the forearm is elevated. Slings which have a soft, fabric envelope do not always adequately support the patient's hand and wrist, especially when the forearm is elevated, since the flexible envelope tends to telescope downward along the forearm. While others do provide support, they do so by rigidly holding the patient's hand in position with a strap. In some cases rigidly holding the hand may perhaps be necessary, but for other cases requiring support only, these slings may be very uncomfortable.

SUMMARY OF THE INVENTION

This invention provides an arm sling which gives substantial support to a patient's elbow, forearm, wrist, and hand without rigidly fixing the patient's hand or wrist in position. The invention permits easy access to the patient's arm while facilitating elevation of the patient's forearm to a number of positions, and at the same time allowing rotation of the patient's upper arm at the shoulder joint.

In accordance with the invention, an improved method and a versatile apparatus for an arm sling is disclosed. The sling includes a semi-rigid or rigid arm support member, which is formed according to one aspect of the invention, from a sheet of flexible plastic material, cardboard, or the like. The arm support member is formed into a trough for supporting the patient's elbow at the proximate end of the trough, and the patient's wrist and forearm at the distal end thereof. The middle portion of the trough supports and partially encircles the patient's forearm, leaving the top of the trough open for easy access. The ends of an adjustable strap are coupled respectively to the middle portion of the arm support member, that is, away from the distal end of the trough and to a point on the arm support member near the patient's elbow at the proximate end of the trough. The strap extends from the middle portion of the trough, over the patient's ipsilateral shoulder, downwardly across the patient's back, and across the front of the patient's upper body to a point on the arm support member near the patient's elbow. The strap thus suspends the patient's arm in the trough formed from the semi-rigid arm support member, in a cantilevered fashion. Adjustment of the strap length provides for elevation of the distal end of the patient's forearm (including his wrist and hand) to a variety of positions. However, the invention leaves such distal end of the trough relatively free for lateral movement, and allows rotation of the patient's upper arm at the shoulder joint.

According to one aspect of the invention, the arm support member has a pair of side portions, to which a yoke is connected. The adjustable strap is then connected to the yoke to support the patient's forearm in a cantilevered fashion, that is, near the middle of the trough and away from the distal end of the trough, while the relatively rigid distal end of the trough provides support for the patient's wrist and hand.

According to another aspect of the invention, an elbow piece is provided for the arm support member. It should be apparent that one of a number of elbow angles is required when using the invention. With this in mind, adjustable means are provided for fixing the elbow piece in position at a particular angle with respect to the arm support member. In a preferred embodiment, these adjustable means include pressure-sensitive engaging means, such as those available under the tradename "Velcro", for adjustably fixing the angle of the elbow piece relative to the trough, and also for adjusting the width of the trough to accommodate the width of the patient's arm.

The cantilevered suspension of the semi-rigid arm trough thus permits the distal end of a patient's arm to be comfortably supported at a point away from the distal end of the trough and provides unencumbered access to the patient's arm. In addition, this invention permits the patient's arm to be elevated to any desired position while still permitting rotation of the arm at the shoulder joint as well as allowing free lateral movement of the arm from a position having the arm extending directly across the patient's body to a position with the arm extending forward and away from the body. The adjustable aspect of the elbow piece also facilitates and improves patient care and comfort.

BRIEF DESCRIPTION OF THE DRAWING

For a more complete understanding of the invention, reference is made to the drawings which form a part of this specification in which.

DETAILED DESCRIPTION OF THE PREFERRED EMBODIMENT

Reference is now made in detail to a preferred embodiment of the apparatus of the invention illustrated in the accompanying drawings, which incorporates the best mode contemplated by the inventor at the time of filing this patent application, of practicing the method and apparatus of the invention.

Figure 1:
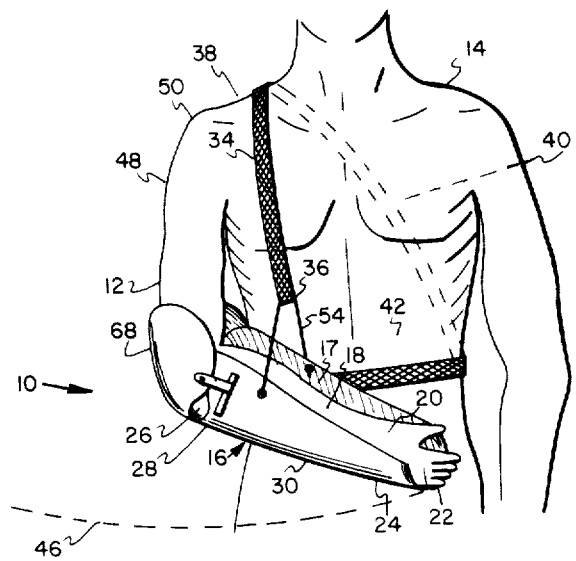
FIG. 1 is a front view of a patient wearing a sling according to the invention.

Referring to the drawings, FIG. 1 shows a sling assembly 10 supporting the arm 12 of a typical patient 14 in one of a number of positions. An arm support member 16 is formed into a trough 17 which partially encircles and supports the patient's forearm 18. Most desirably, support member 16 is a sheet of a semi-rigid (slightly flexible) material, such as of a cardboard or of a vinyl, polyethelene or polypropolene plastic. However, from the broad standpoint it could be of a rigid material formed into a desired shape for supporting a patient's arm.

Figure 2:
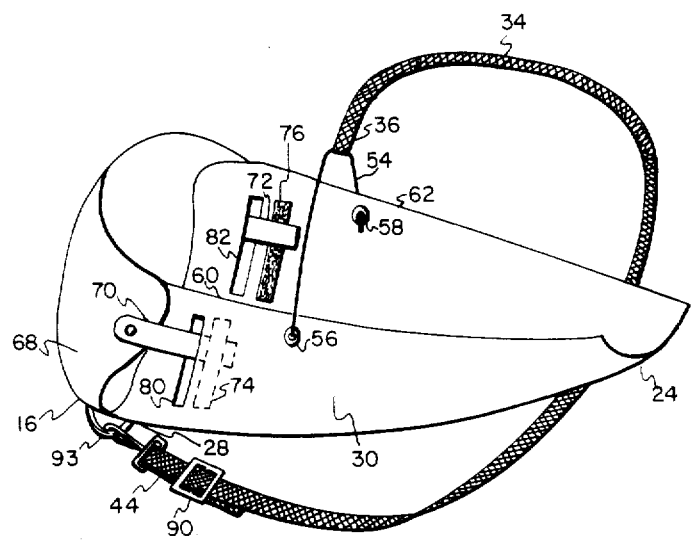
FIG. 2 is a perspective view of a sling with the elements thereof shown arranged for use.

The distal end of the patient's forearm 18, that is, the patient's wrist 20 and hand 22, is supported by the distal end 24 of the trough 17. The patient's elbow 26 is supported by the trough 17 at its proximate end 28. The middle portion 30 of the trough comfortably supports and partially encircles the patient's forearm 18, leaving the area above the patient's arm open to permit easy access for (and to) theraputic devices and the like. FIG. 2 shows on a somewhat larger scale, the trough 17 formed by the arm support member 16.

FIGS. 1 and 2 also show a support strap 34 coupled by means of a yoke strap at one end 36 to the middle portion 30 of the arm support member 16, that is, away from the distal end 24. A major advantage of coupling the support strap 34 at this point is that the patient's wrist and hand are supported in a cantilevered fashion, thereby enabling the freedom and flexibility discussed previously. Another advantage, apparent from FIG. 1, is that the support means for the trough 17 does not interfere with access to the patient's arm or appliances thereon.

The strap 34 extends, as shown, over the patient's ipsilateral shoulder 38, that is, the shoulder to which the arm under treatment is connected, diagonally downwardly across the patient's back 40 and then around and across the front 42 of the patient's upper body. FIG. 2 shows the other end 44 of the strap 34 coupled to the arm support member 16 at the proximate end 28 of the trough 17 near the patient's elbow 26. The strap 34 thus provides support to the patient's forearm 18, as well as to the wrist 20 and hand 22, by suspending the semi-rigid arm support member 16 in a cantilevered fashion from the patient's shoulder 38. The strap is adjustable in length so that the distal end of the patient's arm can be elevated by the trough 17 to a desired, predetermined position as required. When it is adjusted by, for example, tightening, the patient's elbow is brought forward as an anchor point and the trough is simultaneously elevated. The weight of the extremity is distributed by the strap diagonally across the back of the patient.

An arc 46 is included in FIG. 1, indicating that the distal end of the patient's forearm, which includes the wrist 20 and hand 22, is free to move laterally and that the patient's vertically-oriented upper arm 48 can rotate at the shoulder joint 50 while the patient's elbow 26 remains in the same relative location.

FIGS. 1 and 2 show a yoke member, in this preferred embodiment a thin strap 54, having ends 56, 58 thereof attached to respective ones of a pair of side portions, or lateral flaps 60, 62 extending from the arm support member 16 to form opposite sides of the trough 17. The end 36 of the strap 34 is connected to the yoke strap 54 and, as previously described, supports the patient's forearm away from its distal end in a cantilevered fashion, leaving the distal end 24 of the trough 17 free from support means while still providing comfortable support for the patient's forearm, wrist, and hand. It should be noted that the use of yoke strap 54 enhances access to the patient's forearm by elevating the end 36 of the strap 34 from the trough.

FIGS. 1 and 2 show an elbow piece 68 coupled to the arm support member 16. Means for adjustably fixing the elbow piece 68 at various angles with respect to the trough 17 are provided by a pressure-sensitive engaging means. That is, the straps 70, 72 having portions thereon available under the tradename "Velcro" providing hooks which engage looped portions of corresponding strips 74, 76 fixed to the inside surface of the trough 17. The straps 70, 72 extend through corresponding elongated slots 80, 82 formed in the lateral flaps 60, 62. The straps 70, 72 permit the angle of the elbow piece 68 to be adjusted to accommodate various angles of the patient's elbow, which angles correspond to various elevations of the distal end of the patient's forearm. The straps 70, 72 also permit the proximate end 28 of the trough 17 to be adjusted in width to accommodate the width of the patient's arm. The elbow piece 68 provides support to the patient's elbow 26 and upper arm 48.

Figure 3:
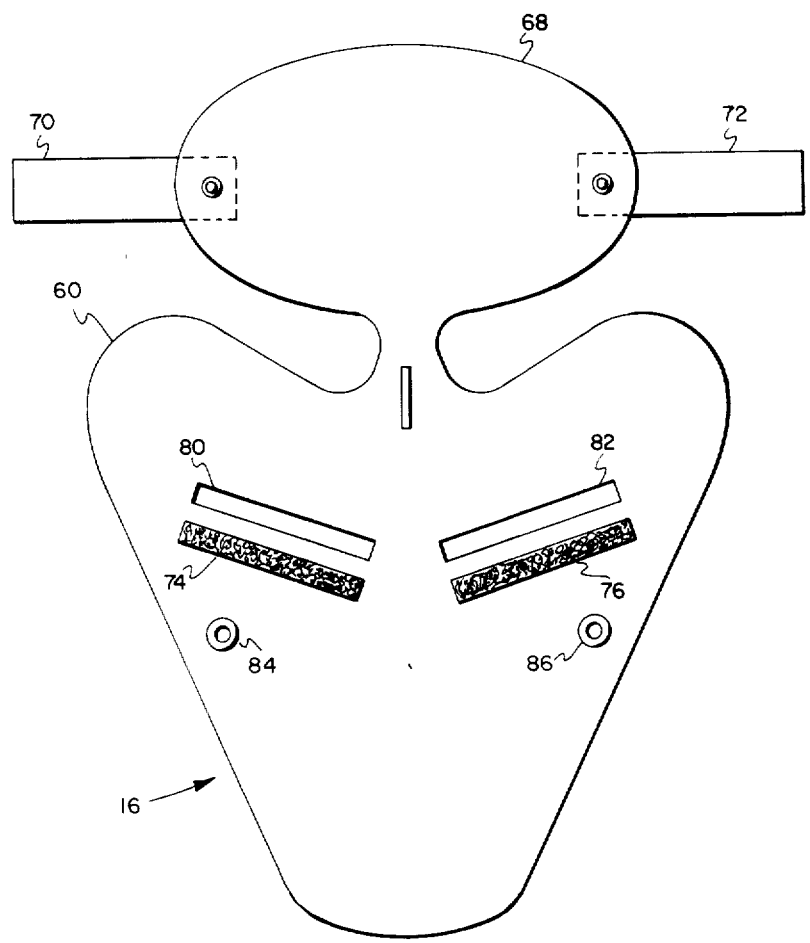
FIG. 3 is a plan view of a one-piece arm support member according to the invention.

FIG. 3 illustrates in plan a preferred embodiment of the semi-rigid arm support member, formed with a symmetrically shaped sheet of plastic material, cardboard, or other suitable material have semi-rigid, flexible characteristics. The arm support member 16 includes the lateral flaps 60, 62 which form the sides for the trough 17. The elongated slots 80, 82 are formed in the flaps 60, 62 and the strips 74, 76 are attached as shown to permit the straps 70, 72, each riveted at one end to the sides of the elbow piece 68, to fix the elbow piece 68 in one of a number of positions. Eyeletted holes 84, 86 are provided on the respective lateral flaps 60, 62, through which the respective ends 56, 58 of the yoke strap 54 extend and are tied, knotted, or otherwise connected for attachment of the yoke strap 54 to the arm support member 16.

Figure 4:
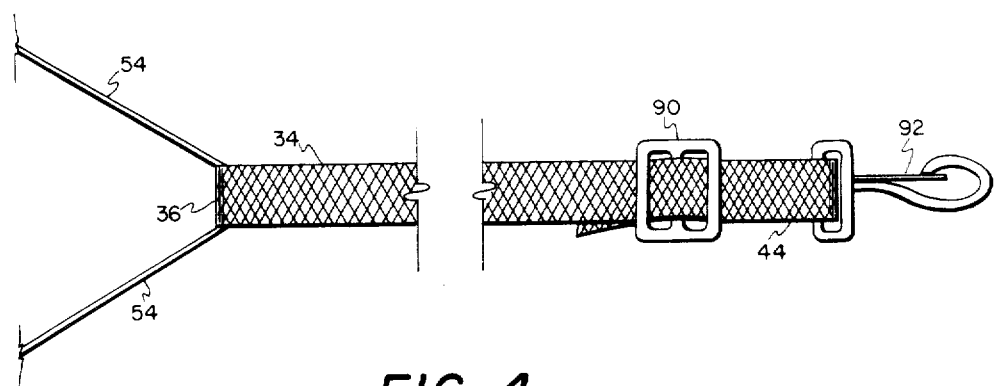
FIG. 4 is a partially cutaway view of a yoke and an adjustable support strap according to the invention.

FIG. 4 shows a fabric strap 34 having attached at one end 36 the yoke strap 54. At the other end 44 is a strap length adjustment buckle 90 and a strap fastener snaphook assembly 92, which fastens to a D-ring 93 (shown in FIG. 2) fastened adjacent the elbow piece to the arm support member 16. By varying the length of the strap 34, the patient's forearm may be elevated to a number of positions depending upon the patient's particular injury or disability. It should be noted that other fastening structures, such as "Velcro" tape, can be substituted for the snaphook D-ring combination 92-93.

FIG. 1 shows the patient's forearm in a position extending slightly below horizontal with the distal end of the arm being free to be moved laterally towards and away from the front 42 of the patient's body, as indicated by the arc 46. The patient's upper arm 48 can also rotate in the shoulder joint 50. The elbow piece 68 is adjusted to accommodate the elbow angle and provide support to the elbow. The strap 34 and yoke 54 suspend the arm from the patient's shoulder 38 in a cantilevered fashion, leaving the forearm, and especially the wrist and hand, well supported by the trough 17 and easily accessible.

Figure 5:
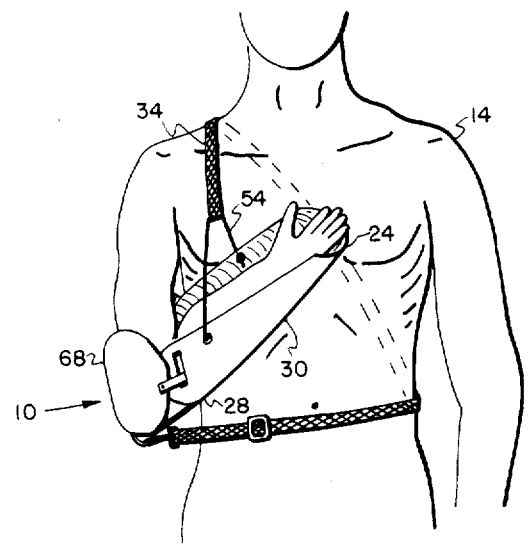
FIG. 5 is a front view of a patient wearing a sling according to the invention with the patient's forearm elevated 45 degrees and extending across the patient's chest.

FIG. 5 shows the patient's forearm in a 45 degree elevated position across the front 42 of the patient's body. The length to the strap 34 is shortened from that shown in FIG. 1 so that the patient's arm is pulled upward the the elbow piece is adjusted as shown. As the strap 34 is shortened, the patient's elbow is pulled forward and the yoke strap 54 pulls upwardly.

Figure 6:
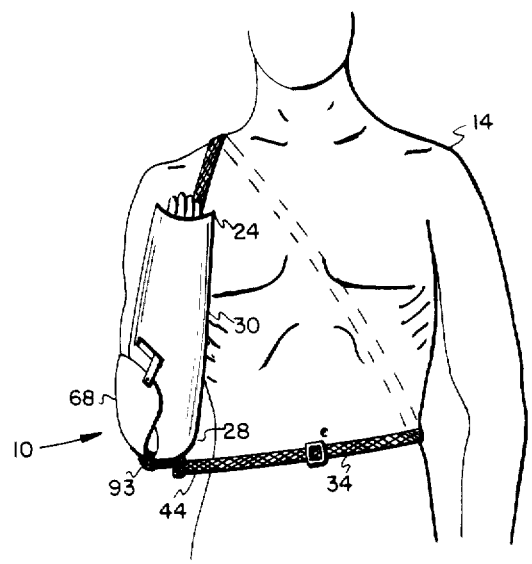
FIG. 6 is a front view of a patient wearing a sling in the elevated position of FIG. 5 but with the arm laterally moved away from the patient's chest.

FIG. 6 shows the patient's arm in the 45 degree elevated position of FIG. 5 but with the arm rotated to the front of the patient.

In summary, it should be appreciated that the invention offers an attractive sling means for supporting a patient's arm at a point away from the distal end of the arm, while still providing comfortable support to the patient's wrist and hand. This is accomplished with the cantilevered support given to the arm with the semi-rigid arm support member depending from the strap provided according to the invention. The invention provides freedom to laterally move the distal end of the patient's arm and rotate the patient's upper arm at the shoulder joint for all arm elevation positions. The open, unencumbered trough design and the adjustable elbow angle are also attractive features of this invention.

Although the invention has been described in connection with one preferred embodiment, it will be appreciated by those skilled in the art that the invention is not limited thereto since various changes and modifications can be made. It is therefore intended that the claims cover any and all such changes and modifications which fall within the true spirit and scope of the basic underlying principles disclosed and set forth herein.

What we claim is:

1. A method of supporting an arm of a patient, comprising the steps of:
    forming a semi-rigid arm support member into a trough having a pair of lateral side portions positioned on each side of the patient's forearm;
    partially encircling the patient's forearm with the trough;
    placing the elbow and distal end of the patient's arm within the trough;
    coupling one end of a strap to the middle portion of the trough and coupling the other end of the strap to the trough near the patient's elbow;
    extending the strap over the ipsilateral shoulder of the patient, diagonally downwardly across the patient's back, and across the front of the patient's body, and adjusting the length of the strap to suspend the trough from the strap and elevate the patient's forearm to a predetermined position while permitting lateral movement of the distal end of the patient's forearm and rotation of the patient's upper arm at the shoulder joint.

2. The method of claim 1 including the steps of attaching the respective ends of a yoke member to one of a pair of lateral side portions of the semi-rigid support member, and suspending the trough with the patient's forearm therein in a cantilevered fashion from the patient's shoulder.

3. The method of claim 1 or claim 2 including adjustably fixing an elbow piece at a predetermined angle to the arm support member to accommodate the angle of the patient's elbow corresponding to elevation of the patient's forearm to the predetermined position.

4. The method of claim 1 or claim 2 including the step of adjustably fixing an elbow piece at the predetermined angle to the arm support member, and adjusting the width of the proximate end of the trough to accommodate the width of the patient's arm with pressure-sensitive engaging means.

* * * * *